US011717006B2

(12) United States Patent
Lukaszewicz et al.

(10) Patent No.: US 11,717,006 B2
(45) Date of Patent: Aug. 8, 2023

(54) METHOD AND SYSTEM OF PROCESSING MEAL FROM OILSEEDS

(71) Applicant: INVENTIONBIO SP. Z O.O., Bydgoszcz (PL)

(72) Inventors: Marcin Lukaszewicz, Wroclaw (PL); Marek Kulazynski, Wroclaw (PL); Anna Krasowska, Wroclaw (PL)

(73) Assignee: INVENTIONBIO SP. Z O.O., Bydgoszcz (PL)

( * ) Notice: Subject to any disclaimer, the term of this patent is extended or adjusted under 35 U.S.C. 154(b) by 667 days.

(21) Appl. No.: 16/606,982

(22) PCT Filed: Apr. 20, 2018

(86) PCT No.: PCT/IB2018/052768
§ 371 (c)(1),
(2) Date: Oct. 21, 2019

(87) PCT Pub. No.: WO2018/193421
PCT Pub. Date: Oct. 25, 2018

(65) Prior Publication Data
US 2020/0187524 A1    Jun. 18, 2020

(30) Foreign Application Priority Data

Apr. 21, 2017    (PL) .......................... 421356

(51) Int. Cl.
*A23K 10/12*    (2016.01)
*A23K 20/189*    (2016.01)
(Continued)

(52) U.S. Cl.
CPC .............. *A23K 10/12* (2016.05); *A23K 10/14* (2016.05); *A23K 10/18* (2016.05); *A23K 10/37* (2016.05); *A23K 20/189* (2016.05); *A23K 40/25* (2016.05); *C12M 29/18* (2013.01); *C12M 43/00* (2013.01); *C12M 45/00* (2013.01); *C12M 47/10* (2013.01); *C12M 47/12* (2013.01); *C12P 1/04* (2013.01)

(58) Field of Classification Search
CPC ............................. C12M 43/00; C12M 45/00
See application file for complete search history.

(56) References Cited

U.S. PATENT DOCUMENTS

| 5,316,782 A   * | 5/1994 | Zimlich, III | ........... A23K 10/38 426/456 |
| 2003/0180897 A1* | 9/2003 | Ulrich | .................... A23K 10/24 435/161 |

(Continued)

FOREIGN PATENT DOCUMENTS

| CN | 102675274 | * | 9/2012 | .............. Y02P 20/10 |
| DE | 3540179 A1 | | 5/1987 | |

(Continued)

*Primary Examiner* — Felicia C Turner
(74) *Attorney, Agent, or Firm* — Craft Chu PLLC; Andrew W. Chu

(57) ABSTRACT

The method and system for processing meal from oilseeds after oil extraction includes biotransformation of meal and its cascade, sequential refining leading to the separation of the product or products with high added value, and finally obtaining the remaining biomass with an increased nutritional value compared to the original post-extraction meal material.

15 Claims, 2 Drawing Sheets

(51) Int. Cl.
   *A23K 40/25*    (2016.01)
   *A23K 10/14*    (2016.01)
   *A23K 10/18*    (2016.01)
   *A23K 10/37*    (2016.01)
   *C12M 1/00*     (2006.01)
   *C12P 1/04*     (2006.01)

(56) References Cited

U.S. PATENT DOCUMENTS

| | | | | |
|---|---|---|---|---|
| 2004/0043451 | A1* | 3/2004 | Yoneda | C12N 1/20 |
| | | | | 435/320.1 |
| 2005/0175734 | A1* | 8/2005 | Angelini | A23L 11/05 |
| | | | | 426/41 |
| 2006/0251761 | A1* | 11/2006 | Jansen | C13K 1/08 |
| | | | | 426/28 |
| 2007/0037267 | A1* | 2/2007 | Lewis | C12P 7/06 |
| | | | | 435/161 |
| 2014/0024064 | A1* | 1/2014 | Burlew | C11B 1/025 |
| | | | | 435/157 |
| 2016/0100619 | A1* | 4/2016 | Patterson | A23J 3/14 |
| | | | | 426/430 |
| 2017/0114371 | A1* | 4/2017 | Pedersen | C12Y 302/01 |

FOREIGN PATENT DOCUMENTS

| | | | | | |
|---|---|---|---|---|---|
| EP | 2514318 | A1 | 10/2012 | | |
| GB | 935075 | A | 8/1963 | | |
| GB | 1472803 | A | 5/1977 | | |
| GB | 1485502 | A | 9/1977 | | |
| WO | WO-2016022779 | A1 * | 2/2016 | ............ | A01N 25/00 |
| WO | WO-2017049394 | A1 * | 3/2017 | ............... | C10L 1/02 |

* cited by examiner

METHOD AND SYSTEM OF PROCESSING MEAL FROM OILSEEDS

CROSS-REFERENCE TO RELATED APPLICATIONS

See also Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The method and system of processing meal from oilseeds.

2. Description of Related Art Including Information Disclosed Under 37 CFR 1.97 and 37 CFR 1.98

The subject of the invention is a method and system for processing meal from oilseeds after oil extraction. Currently, one of the most readily available substrate (biomass) is rapeseed meal. As much as 24% of oilseed flour used as feed comes from rapeseed, compared to 59% from soybean and 12% from sunflower. Compared to soybean meal, the disadvantage of rapeseed meal is that it contains a higher percentage of cell wall polysaccharides, most of which is not digested by endogenous enzymes of monogastric animals. Rapeseed meal, on the other hand, is superior to soy meal with respect to the content of certain amino acids. For example, rapeseed meal contains more methionine and cysteine. Oilseeds contain about 40% oil. After extraction, the meal, apart from hard-absorbed or undigested carbohydrates, may contain between 38% and 43% of protein. Nevertheless, meal often contains anti-nutritional or toxic compounds. For example, rapeseed could be a significant source of protein, to a large extent replacing soy, if it were not for the content of toxic glucosinolates and other anti-nutritional ingredients which can cause thyroid enlargement, liver damage and even animal death. Over the years, the content of glucosinolates in rapeseed cultivars has gradually decreased and is now one order of magnitude smaller. Therefore, feed for broilers and laying hens may now contain up to 20% of rapeseed meal and not cause negative side effects. Creating new varieties is, however, a long-term and very cost intensive process. The phenomenon of biotransformation of biomass to obtain added value is well known; such transformations are used in traditional fermented foods or beverages. The *Bacillus subtilis* var natto strain is used in the preparation of fermented soya-natto products. The proteases secreted by *Bacillus subtilis* (natto) play an important role in the production of natto: they have an optimum activity at pH=8.5 and pH=10.3-10.8. Hydrolysing soy proteins, they contribute to creating a characteristic natto flavour. *B. subtilis* var natto produces subtilisin, an enzyme which degrades an allergen found not only in unfermented, but also in fermented soy products such as, for example, natto. Although *Bacillus subtilis* var natto has been used for the production of valuable human foods for many years, this process has not been used to produce animal feed with increased nutritional value. In particular, *Bacillus subtilis* var natto strains have not been isolated or tested for biotransformation of various products which could be used in animal feeds. The method of production of biosurfactants, substances from the group of lipopeptides, used in the production of household chemicals and cosmetics is known from patent application P.406135. It is characterized by fermentation carried out using the traditional liquid state fermentation method in the pH 7 at 27° C. which provides pseudo-homogeneity of the system, with an appropriate aeration of the culture for 48 hours, in the presence of *Bacillus* microorganisms grown on the medium consisting of post-extraction rapeseed meal mixed with rapeseed cake at the ratio of 1:1.25, in an amount of 19.5 to 35.5 wt. %, then the resulting mixture is supplemented with water in the amount of 60 to 70 wt. % and inoculated with a liquid bacterial culture of *Bacillus*, growing on M9 mineral medium from the night culture. The substances, after fermentation, are purified by reverse osmosis and/or further purified by organic solvent extraction with tert-butyl methyl ether (TBME).

BRIEF SUMMARY OF THE INVENTION

The aim of the invention was to develop a method of biotransformation of meal and its cascade, sequential refining leading to the separation of the product or products with high added value, and finally obtaining the remaining biomass with an increased nutritional value compared to the original post-extraction meal material. The essence of the method, according to the presented invention, is based on the fact that both the meal from oilseed with additives which stimulate the biosynthesis of products are hydrated to a water content of 20% to 85%, using water from a water tank, and inoculated with microorganisms. The oilseed obtained meal is subjected to pre-treatment in the meal components preparation tank, consisting of its sterilization. Then, it is dosed into the bioreactor, in which it is incubated from 6 h to 48 h at temperature in the range of 20° C. to 50° C., and the mixture after fermentation is directed to the separator where the solid fraction is separated from the liquid fraction. The solid fraction is then dried at a temperature not exceeding enzyme denaturing temperature, and then, as a finished product in the form of a bio-meal, it is dispensed into the supplementary feed mixture (SFM) tank. In turn, the liquid fraction goes to the centrifuge, in which microbial cells and solid contaminants with diameters greater than 0.1 μm are centrifuged and reverted back to the bioreactor (as inoculum). The purified liquid fraction is, according to the first option, directed to the absorber in which sorption of the biosurfactant produced by microorganisms is carried out on the activated carbon that has been dried in a dryer prior, while the desorption is carried out by subjecting the sorbent to $CO_2$ extraction under supercritical conditions in a pressure reactor. According to the second option, the purified liquid fraction is extracted in a reactor at the atmospheric pressure. According to the third option, the purified liquid fraction is directed from the centrifuge to precipitation in the reactor or, according to the fourth option, it is concentrated in the evaporator, from which the aqueous solution is directed to the water tank, and the resulting concentrate containing the isolated raw surfactants is directed to the raw surfactants tank. In turn, after the separation of surfactants, the liquid fraction, which contains polymers, is concentrated, the separated water is drained back to the water tank and then, in the polymer separator, polymer is separated in its raw form from concentrated liquid fraction in the presence of ethanol. The raw polymer is then directed to the raw polymer tank, and the liquid fraction is dosed to the ethanol recovery unit. The separated ethanol is again directed to the polymer separator, and the remaining liquid fraction, purified from ethanol, containing bioproducts, is directed to the bioreactor. Finished raw surfactants and raw polymer products are further refined and/or fractionated in a polymer and/or surfactant fractionator using known methods, and directed to the purified surfactin tank, or to the purified polymer tank.

Preferably, rapeseed meal should be the oilseed meal.

Preferably *Bacillus subtilis* natto should be the microorganisms in question.

Preferably, the fermentation process should be carried out under aerobic conditions with the aeration in the amount of 0.01 to 10 volumes of air per volume of bioreactor per 1 minute.

Preferably, the solid fraction, separated after fermentation, should be the probiotic and prebiotic component of the supplementary feed mix (SFM) which is modified using the known methods of sterilization, or extraction, or granulation, or mixing with other additives.

Preferably, the activated carbon should be in granular form.

Preferably, the desorption of surfactants should be carried by rinsing with solvents such as water, ethanol or a mixture of both.

Preferably, the acid precipitation should be used.

Preferably, the activated carbon should be dried to obtain moisture levels equal to the maximum moisture of the meal.

Preferably, the dried activated carbon should be subjected to $CO_2$ extraction under supercritical conditions using such co-solvents as ethanol or methanol, or just ethanol, or methanol without introducing $CO_2$.

Preferably, the liquid fraction, after separating the surfactants containing the polymers in the first stage, should be concentrated by filtration, preferably using a membrane filter.

Preferably, the polymers should be obtained by ethanol precipitation in a weight ratio of 50% to 90%, preferably at a temperature of −15° C. to +20° C.

It is preferred that the supplementary feed mix component has enzymatic activity and is capable of decomposing mycotoxins.

It is preferred that the supplementary feed mix component has mineral chelating properties.

DETAILED DESCRIPTION OF THE INVENTION

Figure 1:
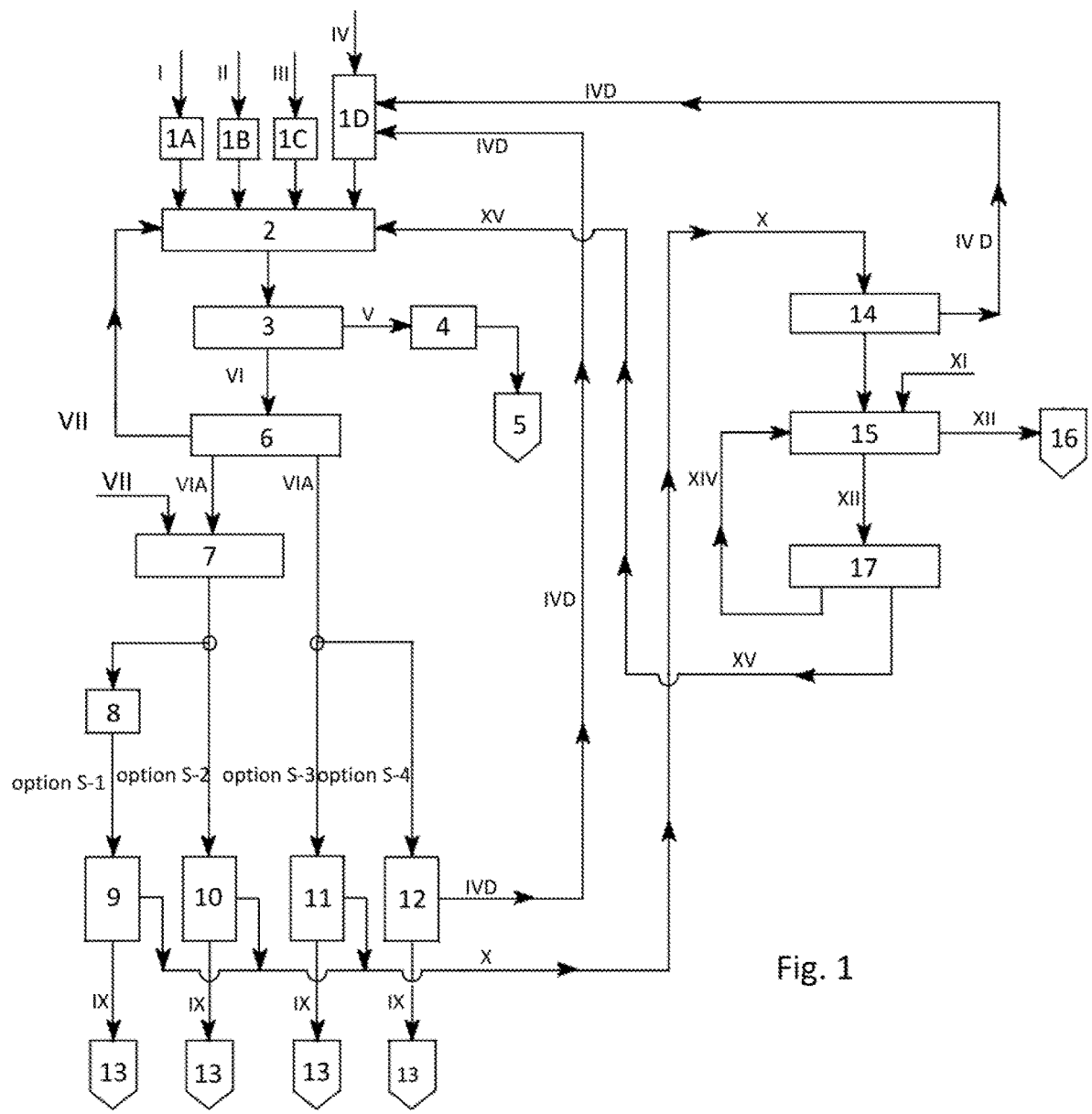
FIG. 1 is a schematic view of the system using oilseed meal to obtain finished products, according to the present invention.

What is important in the system, is that according to the invention, at the gateway to the process there is a micronutrient tank, a meal tank, additives reservoir, a water reservoir, which are connected to a bioreactor which, in turn, is connected to a centrifuge via an extruder and a bacteria discharge conduit, while the extruder is connected to a reservoir of supplementary feed components through a dryer. Further, the centrifuge is connected with a pressure extractor through an absorber and conduits equipped with a valve, or with an extractor at the atmospheric pressure, whereas the pressure extractor is connected through the dryer and the conduit equipped with a valve. The centrifuge is connected to the reactor and dehydrator by conduits equipped with valves. The pressure extractor, the extractor at atmospheric pressure, the reactor, the dehydrator are connected with the raw surfactin tank. Moreover, the pressure extractor, the extractor at atmospheric pressure and the reactor are connected to the polymer separator through an evaporator which is, in turn, connected to the water tank, while the separator of polymers is connected to the raw polymer tank and a device recovering ethanol, which is connected to the polymer separator and the bioreactor via conduits, while the dehydrator is connected to the water tank.

Preferably, the reservoir of raw surfactants and the raw polymers reservoir should be connected to the fractionator, which in turn is connected to the purified surfactin reservoir or the tank of purified polymers. An advantage of the solution, according to the invention, is the capability of obtaining high quality new products such as polymers, bio surfactants. The biomass is used as a supplementary feed mix component with a competitive edge thanks to lower production costs, lower price, uniqueness on the market, and due to production employing environmentally friendly methods. Compared to existing products on the market, these do not contain even a trace amount of harmful substances, such as residues from liquid extraction obtained by various types of solvents. As a result of refining on carbon sorbents, these products are characterized by a very high purity which fosters their use in many food or pharmaceutical and cosmetic preparations. Dedicated sorbents used in the process help reduce energy consumption. In addition, in the processed meal, short organic acids with short chains, for example butyric or lactic acid are produced and introduced into the feed, lowering excessive pH, which will increase the prebiotic function of fructans and surfactants remaining in the feed. Microorganisms which secrete metabolites significantly increase the amount of chelated forms which are better assimilable minerals. A big advantage is the antimicrobial activity of metabolites secreted to meal, e.g. biosurfactants or bacteriocins, protecting animals from *Salmonella* and Enterobacteriaceae poisoning. When feedstuffs with the addition of microorganisms were used to feed poultry, faster weight gain was observed than when using traditional feed, feed intake was reduced, the poultry showed better health, and the emission of gases from those feedstuffs was lower. At the initial stage of chicken development, the increase in body weight was up to 8% more, compared to feeding the chicken with control fodder. The system, according to the invention, allows for the isolation of many bioproducts, such as bio-meal as components of the supplementary feed mixesc with the possibility of its optional supplementation by introducing additives stimulating biosynthesis of products, acquiring surfactin and polymers as shown in the drawing, which shows the system including levan using energy-saving, ecological, waste-free methods. The elasticity of the system is manifested in the fact that different processes of surfactin secretion can be used optionally.

Figure 2:
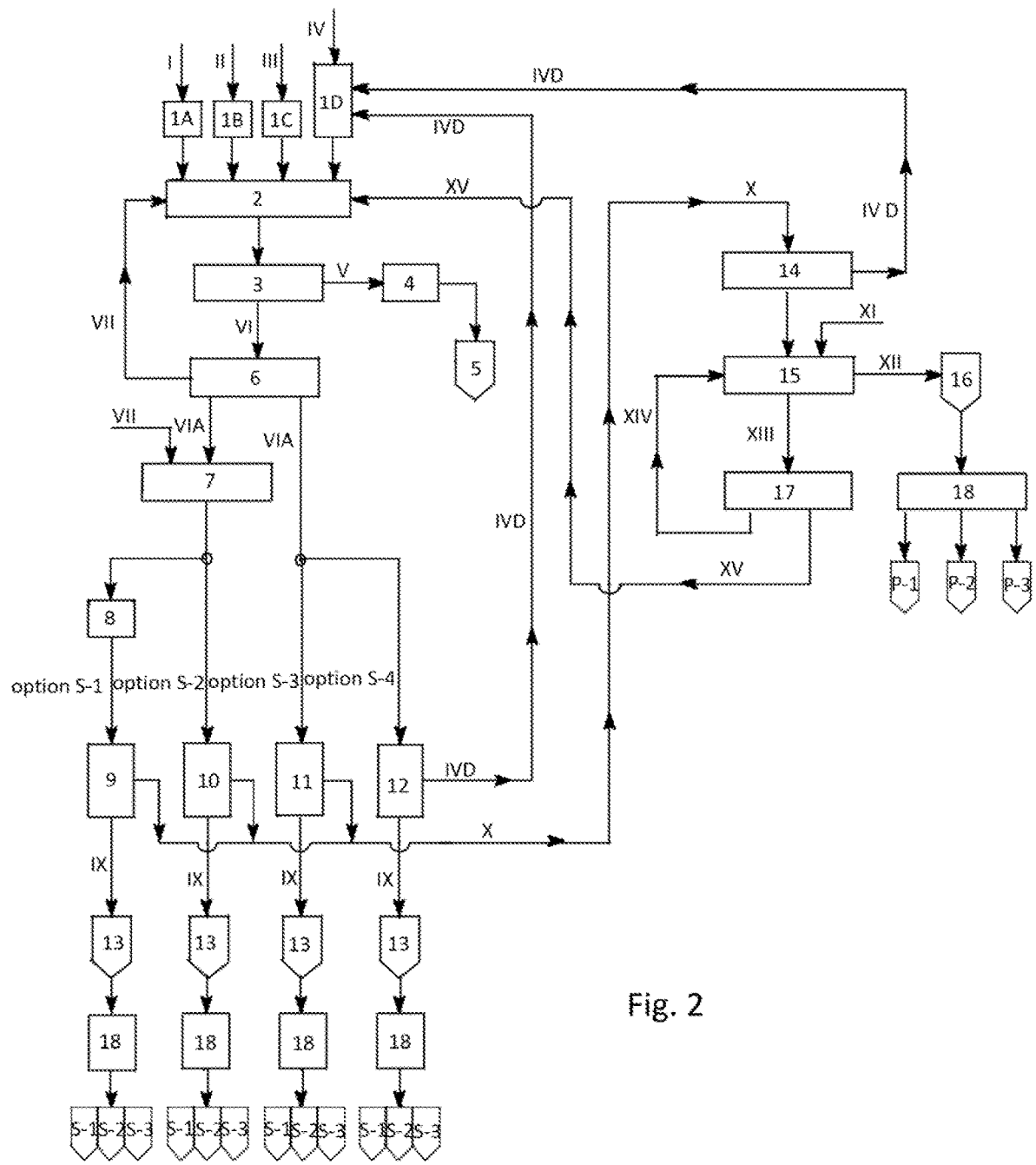
FIG. 2 is a schematic view of the system for obtaining ready-made products, according to the present invention.

The subject of the invention is explained in the example of implementation and shown in the drawing, in which FIG. 1 shows the system using oilseed meal after oil extraction to obtain finished products in the form of a bio-meal, raw surfactin and a raw polymer, and FIG. 2 presents the system for obtaining ready-made products in the form of bio-meal, purified surfactin and purified polymer.

Example 1

The method of processing meal from oilseed after extraction of oil is based on principle that post-extraction meal I I is subjected to sterilization in the meal tank IB, and then mixed at a 50/50 weight ratio with a 24 h *Bacillus subtilis* I culture in the medium containing additives stimulating product synthesis II I with the following composition: −50 g/L of sucrose, −15 g/L of glutamic acid sodium salt, 5 g/L MgSO4, 5 mg/L CuSO$_4$, 3 mg/L Fe$_2$(SO$_4$)$_3$, 15 mg/L MnSO4, 3 g/L KH$_2$PO$_4$, 5 g/L NH$_4$NO$_3$, 1 g/L yeast extract. The resulting mixture is subjected to hydration and subsequent SSF type fermentation in bioreactor 2, at 37° C., under conditions ensuring aeration in an amount of 0.1 volume of air per one bioreactor volume for 1 minute, maintaining constant moisture levels of the substrate by adding water from the water tank ID and/or liquid bio product fractions from the ethanol recovery device 17.

At the end of the fermentation, the solid fraction V is separated from the liquid fraction VI in the separator 3, preferably by press extrusion. The solid fraction V is dried at a temperature not exceeding the value of enzyme denaturation in the bio-meal dryer 4 and, as a finished component of the supplementary feed, is directed to the supplementary feed components tank 5. Thus, obtained solid fraction V is a probiotic and prebiotic feed additive which can be modified using known methods such as: sterilization, extraction, granulation, mixing with other additives with the view to optimising it for a particular group of animals. The supplementary feed mix component has enzymatic properties and the capability of breaking down mycotoxins due to the presence of microorganisms. It also has mineral chelating properties, increasing their bioavailability thanks to metabolites secreted by the microorganisms.

Next, the liquid fraction VI is centrifuged to remove microorganism VII cells and other solid contaminants with diameter sizes exceeding 0.1 μm, which are directed to bioreactor 2. The purified VIA liquid fraction containing biosurfactants is directed to the absorber 7, a column filled with active carbon through which it is passed. The preferred form of activated carbon is granular, characterized by the most developed surface of mesopores, i.e. pores with a width of 2-50 nm. The chemical nature of the sorbent surface should not be alkaline, and the pore surface should be weakly oxidized.

The next step in the process is desorption. The activated carbon after the adsorption process is separated from the solution, dried in the dryer 8 at the temperature not exceeding 80° C., and placed in the pressure extractor 9, in which the extraction is carried out with supercritical fluids. Carbon dioxide in the supercritical state is used as the extractant. Extraction is carried out at 50° C. in an hourly cycle, using 100 cm$^3$ of liquid carbon dioxide per 15 g of activated carbon with approx. 80 mg/g of adsorbed surfactin. Raw surfactin IX is directed to the raw surfactants tank 13 as a finished product. The liquid fraction after removal of raw surfactin X, containing other bioproducts including polymers, is further fractionated in order to separate the polymers from the liquid fraction. In the first stage, the liquid fraction, after the removal of raw surfactin X, is directed to the eveporator 14, in which it is concentrated 4 times, preferably on cross-flow filtration membranes. This process reduces the amount of ethanol necessary for the precipitation of polymers, and the liquid fraction constituting aqueous solution IVD is discharged to the water tank ID. The polymers are precipitated in the polymer separator 15 using ethanol XI with the weight ratio in the range from 50% to 90%, preferably at a temperature from −15° C. to +20° C.

The precipitate of the raw polymer is separated from the liquid fraction for a 24 h sedimentation, and its solid fraction, after separation of polymer XII, is directed to the raw polymers tank 16. The liquid fraction, after polymer XIII separation, together with ethanol and other bioproducts flows through the ethanol recovery device 17, in which ethanol XIV is separated and directed back to the polymer separator 15, while the liquid fraction of the bio-product after evaporation of ethanol XV is fed to the bioreactor 2. Raw surfactants and raw polymers are further refined and fractionated using known methods. This is why the products from the raw surfactant tank 13 or from the raw polymers tank 16 are fractionated in fractionation devices 18 preferably by chromatographic methods, and purified surfactins are directed to S-I, S-2, S-3 tanks, whereas the purified polymers are directed to P-I, P-2, P-3 tanks.

Example 2

To obtain rapeseed meal with an increased nutritional value, surfactants and polymers, the process given in Example 1 was used, the difference being that the carbon dried in the dryer 8, after the sorption of surfactants, undergoes $CO_2$ extraction in supercritical conditions, using co-solvents such as ethanol or methanol or just ethanol or methanol, without $CO_2$.

Example 3

To obtain rapeseed meal with an increased nutritional value, surfactants and polymers, the process given in Example 1 was used, the difference being that in the 10, solvent desorption is carried out at atmospheric pressure, preferably using anhydrous ethanol.

Example 4

To obtain rapeseed meal with an increased nutritional value, surfactants and polymers, the process given in Example 1 was used, the difference being that precipitation method was used to precipitate the surfactants, and the liquid fraction of VIA bio surfactants was directed to reactor 11 straight from centrifuge 6. Precipitation was carried adding HCl to obtain pH 4.

Example 5

To obtain rapeseed meal with an increased nutritional value, surfactants and polymers, the process given in Example 1 was used, the difference being that the liquid fraction of VIA biosurfactants was directed to the dehydrating device 12, in which the release of surfactants was carried out at 50° C., and then directed to the raw surfactants tank 13, and the aqueous solution IV D was directed to water tank 4.

Example 6

The system for processing meal acquired from oilseeds after oil extraction has, at its inlet, the micronutrient tank 1A, the meal tank IB, the additives tank 1C, the water tank 1D, which are connected by conduits with the bioreactor 2 which, in turn, is connected to the centrifuge 6 through the extruder 3 and the conduit VII. The extruder 3, on the other hand, is connected to the dryer 4 and the supplementary feed components tank 5, while the centrifuge 6 is connected via the absorber 7 and conduits equipped with a valve to the pressure extractor 9, or to the extractor at the atmospheric pressure 10, whereas the pressure extractor 9 is connected with a conduit equipped with a valve through the dryer 8, and the centrifuge 6 is connected to the reactor 11 and the dehydrator 12 via conduits equipped with valves, each of which is, in turn, connected to the raw surfactant tank 13. Moreover, the pressure extractor 9, the extractor at atmospheric pressure 10, and the reactor 11 are connected to a polymer separator 15 via the thickener 14, which is connected to the water tank 1D, while the polymer separator 15 is connected to the raw polymer tank 16 and to the ethanol recovery device 17 which is connected to the polymer separator 15 and the bioreactor 2, while the dehydrator 12 is connected to the water tank 1D.

Example 7

The system for processing meal acquired from oilseeds after oil extraction built as in example 6, except for the raw surfactant tank 13 is connected to the purified surfactin tanks (S-I, S-2, S-3) through the fractionation device 18, and the raw polymer tank 16 is connected to the purified polymer tanks (P-I, P-2, P-3) through the fractionation device 18.

LIST OF MARKINGS

1A—Microelement tank
IB—Meal tank
1C—Additives tank 1C
ID—Water tank
2—Bioreactor
3—Separator for liquid fraction separation
4—Bio-meal dryer
5—Supplementary feed component tank
6—Centrifuge
7—Absorber
8—Dryer
9—Pressure extractor
10—Atmospheric pressure extractor
11—Reactor
12—Dehydrator
13—Raw surfactant tank
14—Evaporator
15—Polymer separator
16—Raw polymer tank
17—Ethanol recovery device
18—Polymer fractionation device
S-I
S-2—Purified surfactin tanks
S-3
P-I
P-2—Purified polymer tanks
P-3
I—Microorganisms
II—Meal
III—Additives stimulating product synthesis
IV—Water
IVD—Water after the process of densification of the liquid polymer fraction
V—Solid fraction of biosurfactants
VI—Liquid fraction of biosurfactants
VI A Liquid fraction of biosurfactants cleaned from microorganisms
VII—Cells of the microorganisms
VIII—Activated carbon
IX—Raw surfactant
X—Liquid fraction after removal of surfactants
XI—Ethanol
XII—Solid fraction after polymer separation
XIII—Liquid fraction after polymer separation
XIV Recovered ethanol
XV Liquid fraction of bioproduct after ethanol evaporation.

We claim:
1. A method of processing meal obtained from oilseed after oil extraction using biotransformation, the method comprising the steps of:
   pretreating oilseed obtained meal in a meal tank;
   mixing said oilseed obtained meal after the step of pretreating, additives stimulating biosynthesis of products, water from a water tank, and microorganisms to water content of 20% to 85% in a bioreactor, said microorganisms being bacteria;
   incubating in said bioreactor from 6 to 48 hours at 20 to 50 degrees Celsius so as to ferment and form a mixture being comprised of a liquid fraction and a solid fraction;
   directing the mixture to a separator;
   separating said solid fraction with said separator;
   drying said solid fraction at a temperature not exceeding denaturalization temperature of enzymes with a bio-meal dryer so as to form a dried solid fraction;
   dispensing said dried solid fraction into a supplementary feed mix component tank;
   separating said liquid fraction with said separator;
   centrifuging said liquid fraction with a centrifuge so as to separate microorganism cells and solid impurities of diameter sizes greater than 0.1 μm from a purified liquid fraction in said liquid fraction;
   directing said microorganism cells and solid impurities of diameter sizes greater than 0.1 μm back to said bioreactor;
   directing said purified liquid fraction for further separation processing,
   wherein further separation processing is comprised of at least one of a first option, a second option, a third option, and a fourth option,
   wherein said first option is comprised of the steps of:
      directing said purified liquid fraction to an absorber;
      carrying out sorption of bio surfactants produced by microorganisms on activated carbon so as to generate adsorbed bio surfactants;
      drying in a dryer, after the step of carrying out sorption; and
      carrying out desorption of said adsorbed bio surfactants by $CO_2$ extraction under supercritical conditions of activated carbon with said adsorbed bio surfactants, in a pressure reactor, so as to generate separated raw surfactant solid fraction and a surfactant separated liquid fraction,
wherein said second option is comprised of the steps of:
directing said purified liquid fraction to an absorber;
carrying out sorption of bio surfactants produced by microorganisms on activated carbon; and
extracting in a reactor at atmospheric pressure so as to generate said separated raw surfactant solid fraction and said surfactant separated liquid fraction,
wherein said third option is comprised of the steps of:
directing said purified liquid fraction to another reactor; and
precipitating said separated raw surfactant solid fraction in said surfactant separated liquid fraction, and
wherein said fourth option is comprised of the steps of:
directing said purified liquid fraction to a dehydrator;
dehydrating so as to generate said separated raw surfactant solid fraction and said surfactant separated liquid fraction; and
directing an aqueous solution to said water tank;
directing said separated raw surfactant solid fraction to a raw surfactant tank;
directing said surfactant separated liquid fraction to a condenser, said surfactant separated liquid fraction containing polymers;
concentrating said surfactant separated liquid fraction so as to generate a concentrated liquid fraction;
directing said concentrated liquid fraction from said condenser to a polymer separator;
separating polymers from said concentrated liquid fraction with ethanol in said polymer separator so as to generate a raw polymer form and a raw polymer separated liquid fraction;
directing said raw polymer form to a raw polymer tank;
dispensing said raw polymer separated liquid fraction dispensed to an ethanol recovery device;
separating ethanol from said raw polymer separated liquid fraction with said ethanol recovery device so as to generate separated ethanol and ethanol pure liquid fraction containing bioproducts;
directing said separated ethanol to said polymer separator;
directing said ethanol pure liquid fraction to said bioreactor;
directing said raw surfactants from said raw surfactant tank to purified surfactin tanks so as to refine said raw surfactants; and
directing said raw polymer form from said raw polymer tank to purified polymer tanks in a polymer fractionation device and/or surfactant fractionation device.

2. The method of processing meal, according to claim 1, wherein said oilseed obtained meal is comprised of rapeseed meal.

3. The method of processing meal, according to claim 1, wherein said microorganisms are comprised of *Bacillus subtilis* natto.

4. The method of processing meal, according to claim 1, wherein the step of incubating in said bioreactor is under aeration conditions of 0.01 to 10 volumes of air per a volume of bioreactor for 1 minute.

5. The method of processing meal, according to claim 1, further comprising the step of:
modifying said dried solid fraction in said supplementary feed mix component tank so as to generate a supplementary feed mix, said dried solid fraction being comprised of a probiotic and prebiotic component of said supplementary feed mix,
wherein the step of modifying said dried solid is comprised of at least one of a group consisting of: sterilizing, extracting, granulating, and mixing with other additives.

6. The method of processing meal, according to claim 1, wherein said activated carbon in said absorber is in granular form.

7. The method of processing meal, according to claim 1, wherein the step of carrying out desorption of adsorbed bio surfactants in said first option is comprised of the follow step:
washing with a solvent, wherein said solvent is selected from a group consisting of water, ethanol, and a mixture of water and ethanol.

8. The method of processing meal, according to claim 1, wherein the step of carrying out desorption of adsorbed bio surfactants in said first option is comprised of the step of:
using acid precipitation.

9. The method of processing meal, according to claim 1, wherein the step of drying in said dryer in said first option is comprised of the step of:
drying said activated carbon to moisture levels equal to a maximum moisture of said oilseed obtained meal.

10. The method of processing meal, according to claim 9, wherein the step of carrying out desorption of adsorbed bio surfactants in said first option is comprised of the step of:
subjecting said dried activated carbon to $CO_2$ extraction under supercritical conditions using a co-solvent, said co-solvent being comprised of ethanol or a mixture of ethanol and methanol.

11. The method of processing meal, according to claim 1, the step of concentrating said surfactant separated liquid fraction X is comprised of the step of:
filtering with a membrane filter.

12. The method of processing meal, according to claim 1, wherein the step of separating polymers from said concentrated liquid fraction is at a temperature of −15 to +20 degrees Celsius, said ethanol having a weight ratio of 50-90%.

13. The method of processing meal, according to claim 5, further comprising the step of:
decomposing mycotoxins with said supplementary feed mix having enzymatic properties.

14. The method of processing meal, according to claim 5, further comprising the step of:
chelating minerals with said supplementary feed mix.

15. The method of processing meal, according to claim 1, wherein the step of pretreating said oilseed obtained meal is comprised of the step of sterilizing said oilseed obtained meal.

* * * * *